United States Patent [19]
Mikhail

[11] Patent Number: 5,755,720
[45] Date of Patent: May 26, 1998

[54] METHOD AND APPARATUS FOR PERFORMING HIP PROSTHESIS SURGERY

[76] Inventor: W. E. Michael Mikhail, 4203 Shamley Green, Toledo, Ohio 43623

[21] Appl. No.: 778,517

[22] Filed: Jan. 3, 1997

[51] Int. Cl.⁶ .................................................. A61B 17/56
[52] U.S. Cl. .............................. 606/94; 606/92; 623/22
[58] Field of Search ............................. 606/94, 93, 92, 606/95, 86; 623/22, 23

[56] References Cited

U.S. PATENT DOCUMENTS

| | | | |
|---|---|---|---|
| 4,399,814 | 8/1983 | Pratt, Jr. et al. | 606/94 |
| 4,454,612 | 6/1984 | McDaniel et al. | |
| 4,491,987 | 1/1985 | Park | |
| 4,650,489 | 3/1987 | Thompson | 623/16 |
| 4,735,625 | 4/1988 | Davidson | |
| 4,815,454 | 3/1989 | Dozier, Jr. | |
| 4,896,662 | 1/1990 | Noble | 606/94 |
| 4,919,153 | 4/1990 | Chin | |
| 4,986,826 | 1/1991 | Roger | |
| 5,047,035 | 9/1991 | Mikhail et al. | |
| 5,061,287 | 10/1991 | Feiler | |
| 5,171,288 | 12/1992 | Mikhail et al. | |
| 5,326,376 | 7/1994 | Warner et al. | 623/23 |
| 5,385,566 | 1/1995 | Ullmark | 606/95 |
| 5,443,523 | 8/1995 | Mikhail | 623/23 |
| 5,665,121 | 9/1997 | Gie et al. | 623/16 |

*Primary Examiner*—Guy V. Tucker
*Attorney, Agent, or Firm*—Emch, Schaffer, Schaub & Porcello, Co., L.P.A.

[57] ABSTRACT

A method and apparatus for performing hip surgery utilizes a preformed sleeve formed of bone cement material and having apertures which is positioned in the femoral cavity. Fresh bone cement is injected under pressure to fill the femoral cavity including the apertures and any spaces or voids between the preformed sleeve and the wall of the cavity. A femoral prosthesis having a stem portion is implanted therein. The interior wall of the sleeve is larger than the stem exterior wall portion encircled by the sleeve such that fresh bone cement is between the interior wall of the sleeve and the stem.

29 Claims, 8 Drawing Sheets

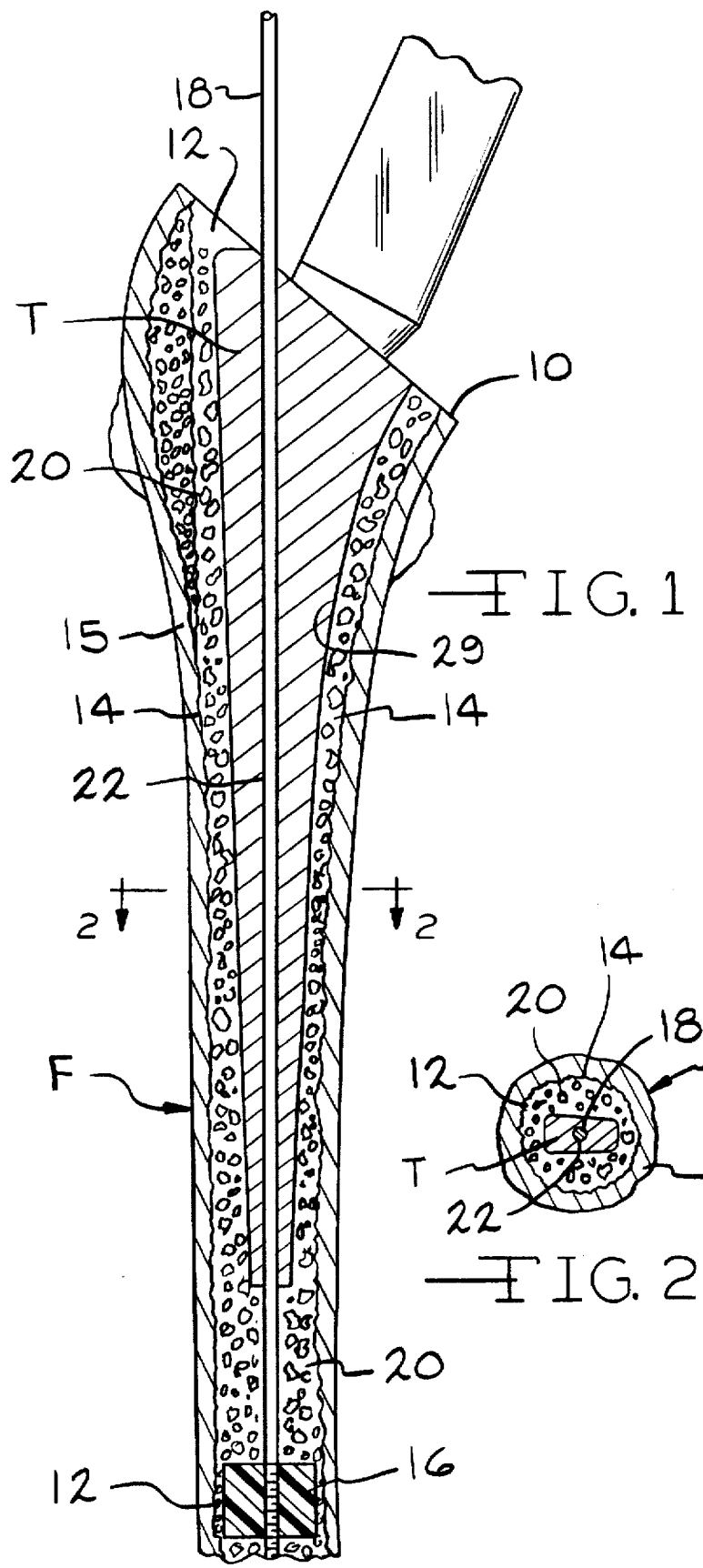

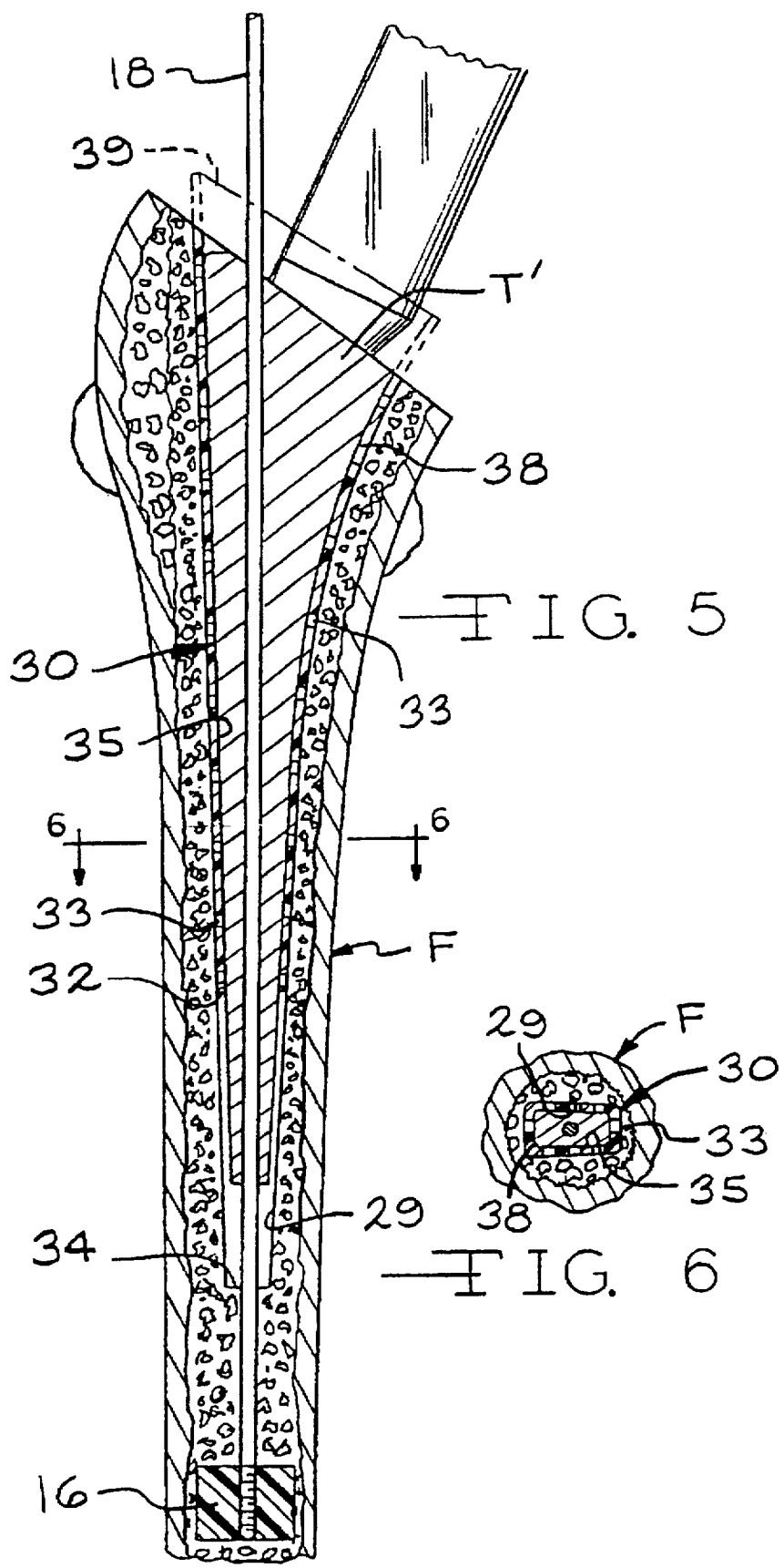

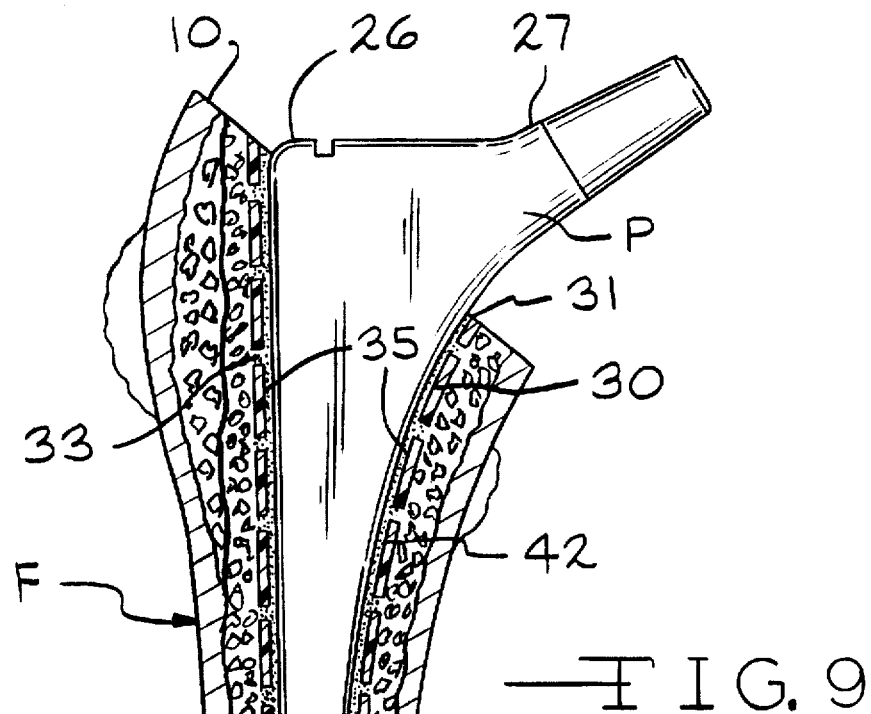
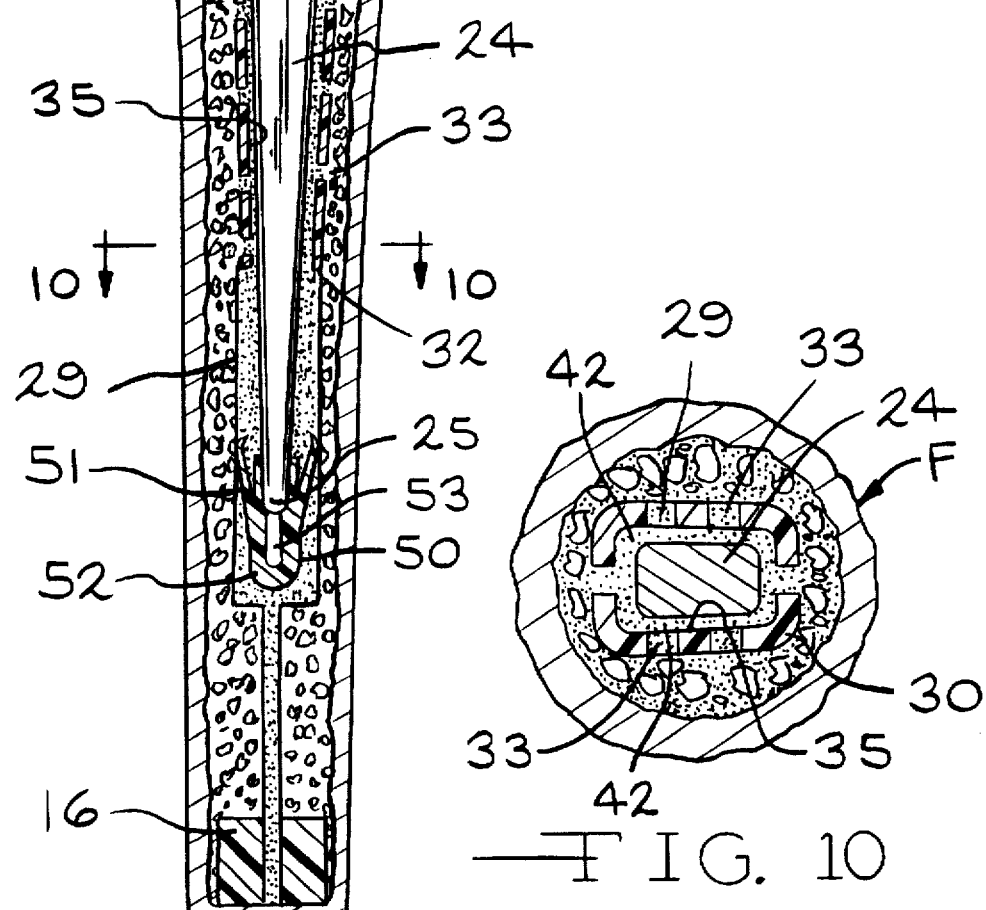
FIG. 9
FIG. 10

METHOD AND APPARATUS FOR PERFORMING HIP PROSTHESIS SURGERY

BACKGROUND ART

The present invention is directed to a method for performing hip surgery and to apparatus for use therein. The broad concept is applicable both to primary hip surgery and to revision surgery in which a hip prosthesis having a stem portion previously implanted in the intramedullary canal of a femur is replaced.

In the course of hip revision surgery, it is necessary to remove the femoral component including its stem from the intramedullary canal of the femur. If bone cement material was used to fix the stem within the intramedullary canal, it must also be removed prior to implantation of the new prosthesis therein. Removal of the cement is accomplished by drilling, reaming and/or removal piecemeal together with any membrane or particulate debris. During such drilling or reaming procedure, it is important that the drill or reamer be properly aligned and guided to assure proper positioning of the prosthesis and to avoid accidental perforation of the cortex of the femur. Systems for assuring tightness desired for optimum grafting with the remaining bone while at the same time forming a new cavity of the desired shape and size to receive the new prosthesis with the appropriate amount of bone cement are well known in the prior art. Proper alignment of a drill reamer are disclosed in the following U.S. Patents of which I am a co-inventor: U.S. Pat. Nos. 5,047,035 and 5,108,405. In compacting the bone graft material used in revision surgery, the surgeon may utilize the cannulated tamp and guidewire described in U.S. Pat. Nos. 5,192,283 and 5,470,336 of which I am also a co-inventor. In addition, I am the inventor or co-inventor of the following patents directed to preformed cement mantles for use on the stem of a hip joint prosthesis implanted in a femur: U.S. Pat. Nos. 5,080,680; 5,171,288; 5,314,493 and 5,443,523. Such patents are incorporated by reference.

DISCLOSURE OF THE INVENTION

The present invention is directed to hip surgery in which the prosthesis is implanted using bone cement. Ideally, it is desirable that all portions of the prosthetic stem implanted in the intramedullary canal have approximately two to three millimeters (2–3 mm) of bone cement separating the implanted stem from the bone. The invention is applicable to primary as well as revision surgery.

Under the present invention, a preformed sleeve of bone cement such as polymethylmethacrylate (PMMA) having apertures is positioned in an oversized cavity prepared in the femoral intramedullary canal and then additional bone cement is injected under pressure into the prepared cavity to substantially fill such cavity. The additional bone cement passes through the apertures of the sleeve filling any gaps between the preformed sleeve and the bone and penetrating a short distance into the compacted cancellous bone graft material in the case of revision surgery or into cancellous spongy bone lining the femoral cortex defining the prepared oversized cavity in the case of primary surgery.

In the case of hip revision surgery, following removal of the old cement and any cement restricter or plug which may have been used, the cavity remaining in the femur will be substantially larger than is necessary or desirable to accommodate the new femoral hip prosthesis. Accordingly, it is generally accepted procedure to place crushed cancellous bone graft in the enlarged cavity or femoral canal. The reason for this is that regenerated bone from the bone graft material, over a long term, is biologically sound and preferred to simply using a great thickness of bone cement to fill the enlarged cavity in supporting the prosthesis. Thus, if the bone cement is thicker than about 6 mm, it is susceptible to cracking. In contrast, incorporated or regenerated bone from the tightly compacted bone graft offers biological bony reconstruction with longer survivability and stronger durability.

In those cases where the crushed cancellous bone graft is used, it is tamped in order to compact it and have it tightly packed in the neo-medullary femoral canal. Under my prior U.S. Pat. Nos. 5,192,283 and 5,470,336, a cannulated tamp is used to compact crushed cancellous bone graft placed in the enlarged cavity resulting from removal of the previously implanted femoral prosthesis and any old bone cement.

Irrespective of whether the patient is undergoing primary or revision surgery, once the cavity is prepared, the apertured sleeve is positioned therein and then the additional bone cement is introduced under pressure by using the appropriate proximal femoral seal. After the introduction of the additional bone cement under pressure, the hip joint prosthesis is implanted within the new bone cement, in generally spaced relationship with the sleeve. Since the sleeve and the new bone cement are preferably manufactured from the same material, for example, PMMA, the new bone cement will bond uniformly with the sleeve as long as there is no blood, marrow fat or other fluid medium between the sleeve and the new cement.

In contrast to my prior patents in which the preformed cement mantles were designed to snugly engage the stem of the associated hip joint prosthesis, the present invention utilizes a sleeve having a thickness of ½ to 2 mm and an interior size larger than the hip joint prosthesis by an amount such that the stem of the prosthesis implanted in the prepared cavity using bone cement will be spaced from the interior surface of the sleeve approximately 2 to 3 mm thereby allowing fresh bone cement to encircle the stem. The exterior surface of the sleeve is in contact with the interior wall of the prepared cavity and thereby assists in stabilizing such cavity interior wall during the insertion of bone cement under pressure and insertion of the prosthesis stem. The sleeve is particularly beneficial in stabilizing the compacted bone graft used in revision surgery. However, it is also helpful in stabilizing the interior wall of the prepared cavity in primary hip surgery, particularly spongy bone in persons with osteoporosis. It insures that the bone cement being injected under pressure does not cause any such spongy bone at the cavity interior wall to be adversely displaced. The holes or perforations in the sleeve will allow the pressurized fresh cement to penetrate the cancellous bone in primary hip surgery and the bone graft in revision hip surgery. The sleeve and the fresh cement including the cement which passes through the sleeve's perforations will form an inseparable cement mantle surrounding the stem and thus guarding against cement defects and the resultant osteolysis with the eventual loosening and stem failure. The total thickness of the cement mantle including the sleeve is approximately 2 to 3 mm.

The invention will be more fully understood and other objects and advantages will become apparent from the following detailed description in conjunction with the attached drawings.

BRIEF DESCRIPTION OF THE DRAWINGS

FIG. 1 is an elevational view, partly in section, showing an oversized cannulated tamp or trial femoral component used in revision surgery following compaction of bone graft material to form a cavity sized to receive a preformed sleeve and femoral hip joint prosthesis.

FIG. 2 is a sectional view taken through line 2—2 of FIG. 1.

FIG. 5 is an elevational view, partly in section, showing placement of the preformed sleeve in the prepared cavity using a cannulated tamp and guide wire.

FIG. 6 is a sectional view taken through line 6—6 of FIG. 5.

FIG. 9 is an elevational view, partly in section, showing a femoral hip joint prosthesis implanted in the cavity.

FIG. 10 is a sectional view taken through line 10—10 of FIG. 9.

BEST MODE OF CARRYING OUT INVENTION

Figure 3:
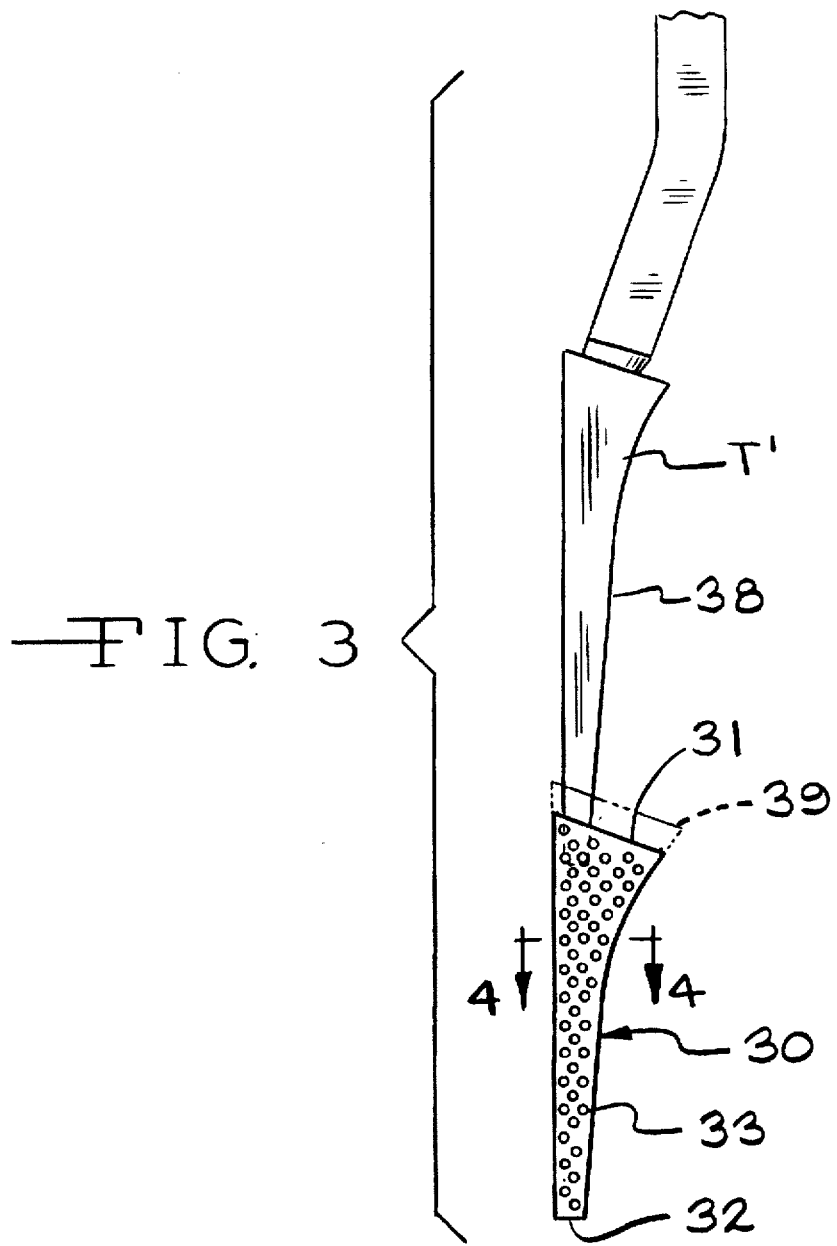
FIG. 3 is an exploded view showing a tamp about to be inserted in the tapered preformed sleeve.

Referring now to FIGS. 1 and 2, there is shown a femur generally designated by the letter F which has had removed therefrom a previously implanted hip joint prosthesis. As shown in FIGS. 1 and 2, the femur F extends from a proximal end 10, which has been cut, toward a distal end (not shown) and has had formed therein an enlarged cavity 12 defined by the interior surface 14 of the cortex 15. The cavity 12 extends from the proximal end 10 toward the distal end a distance which exceeds the length of the femoral hip joint prosthesis to be implanted. The cavity 12 is formed by reaming the old bone cement and/or cortex following removal of the previously implanted prosthesis. Upon the completion of reaming the cavity 12, a plug cement restrictor 16 is positioned in the distal end of the cavity 12. Thereafter, according to the inventions described in U.S. Pat. Nos. 5,192,283 and 5,470,336, a guide wire 18 may be threadedly engaged to the cement restrictor 16.

Figure 8:
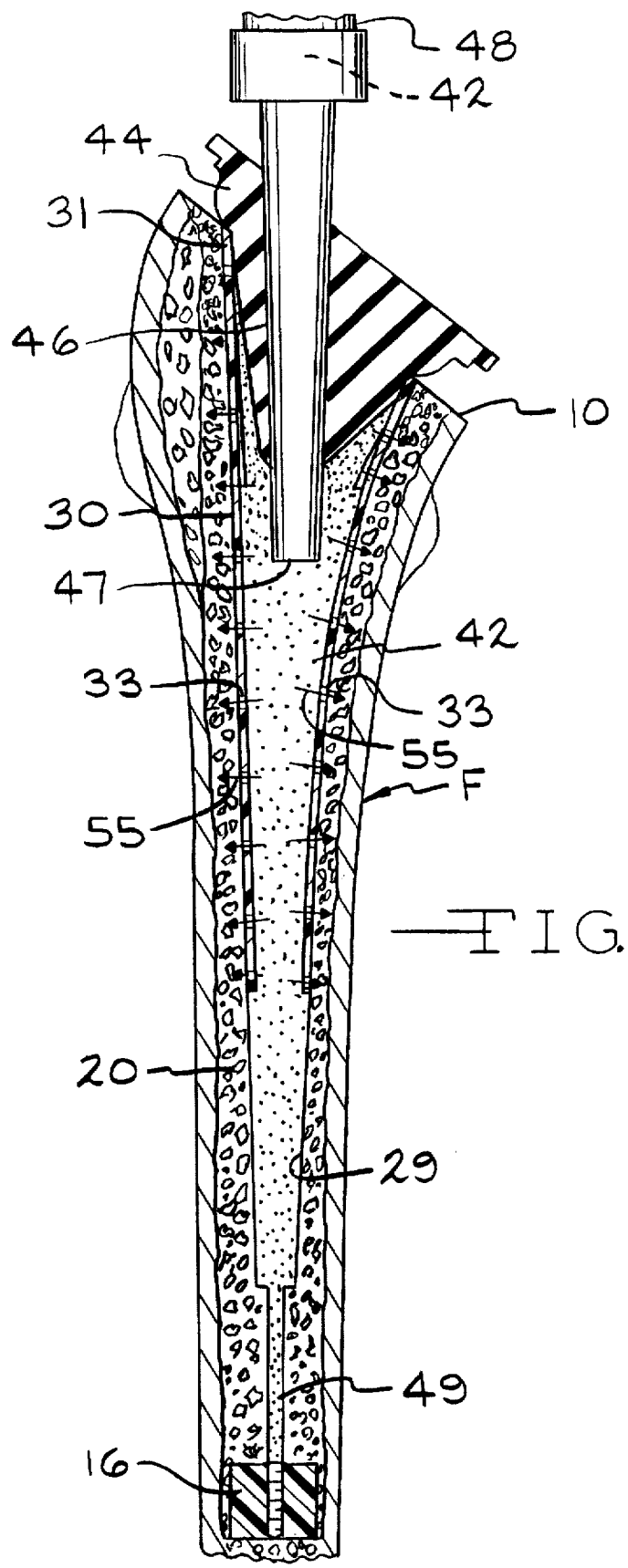
FIG. 8 is an elevational view, in section, of the prepared femoral cavity with the sleeve positioned therein and showing apparatus for injecting fresh bone cement under pressure into the prepared cavity.

Cancellous bone graft material 20 is positioned in the cavity 12 and is compacted to the proper density by means of a cannulated tamp T having a passageway 22 through which the guide wire 18 passes as the tamp T is positioned over such guide wire 18 and inserted into the cavity 12 to compact the bone graft 20 to the appropriate density and form to receive a new femoral hip joint prosthesis P shown in FIG. 8.

Referring to FIGS. 9 and 10, the prosthesis P has a stem 24 which extends from a distal end 25 toward the proximal end 10 of the femur to an enlarged shoulder 26 and a neck portion 27 disposed at an obtuse angle relative to the stem 24.

As may be seen by comparing FIGS. 1 and 2 with FIGS. 9 and 10, the tamp T has a size which is larger than the size of the prosthesis P intended for implantation in the particular patient. The tamp T thus forms a compacted cavity 29 defined by the exterior surface of the tamp T which is larger than the size of the prosthesis intended for implantation by an amount which will provide a total thickness of bone cement of 2 to 3 mm around all portions of the implanted stem 24 encircled by the sleeve. There could be as much as 5 to 6 mm of bone cement medially in the calcar region. The tamp is approximately 20 mm longer than the corresponding stem 24.

Figure 4:
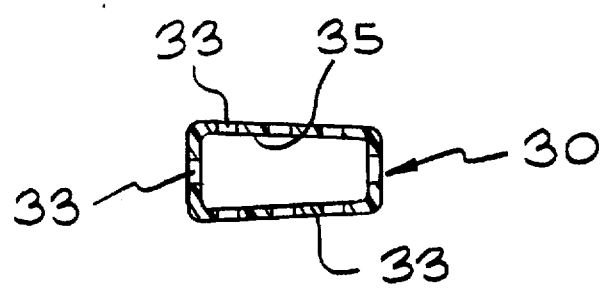
FIG. 4 is a sectional view of the tapered preformed sleeve taken through line 4—4 of FIG. 3.

Referring now to FIGS. 3 and 4, there is shown a preformed sleeve 30 manufactured from a suitable bone cement such as PMMA which extends from a proximal end 31 to a distal end 32 and has formed therein a plurality of apertures 33. The apertures 33 are preferably circular and have a diameter on the order of 1 to 3 mm. The sleeve 30 has a thickness on the order of ½ to 2 mm and has an exterior size and shape permitting it to be snugly received in the compacted cavity 29 from the proximal end 31 to the distal end 32.

Under one alternative embodiment, the sleeve extends higher than the area designated as the proximal end 31 to form an extension 39 shown in dashed lines in FIGS. 3 and 5.

In order to position the sleeve 30 in the compacted cavity 29, it is desirable to position the sleeve 30 on a tamp having a cannulation which may utilize the guide wire 18 for assistance in positioning. The tamp is preferably polished metal. As will be appreciated, since the exterior surface of the sleeve 30 is intended to be in closely conformed contact with the compacted cavity 29, it will have a shape and size which conforms to the exterior surface of the tamp T from the proximal end toward the distal end 25. Due to the thickness of the wall of the sleeve 30 of ½ to 2 mm, the interior surface 35 will have a slightly different shape and size from that of the tamp T. Accordingly, it is desirable to utilize a slightly smaller tamp T' which has an exterior surface 38 shaped and sized to receive the sleeve 30 such that all portions of the interior surface 35 of the sleeve 30 are engaged to the exterior surface of the tamp T'.

As can be seen from viewing FIG. 5, the length of the sleeve 30 is such that the distal end 32 is spaced from the distal end 34 of the compacted cavity 29. The reason for this is to provide an opening at the distal end 32 of the sleeve 30 sufficiently large to permit insertion therethrough of a centralizer 50 such as that shown in FIG. 9.

Figure 7:
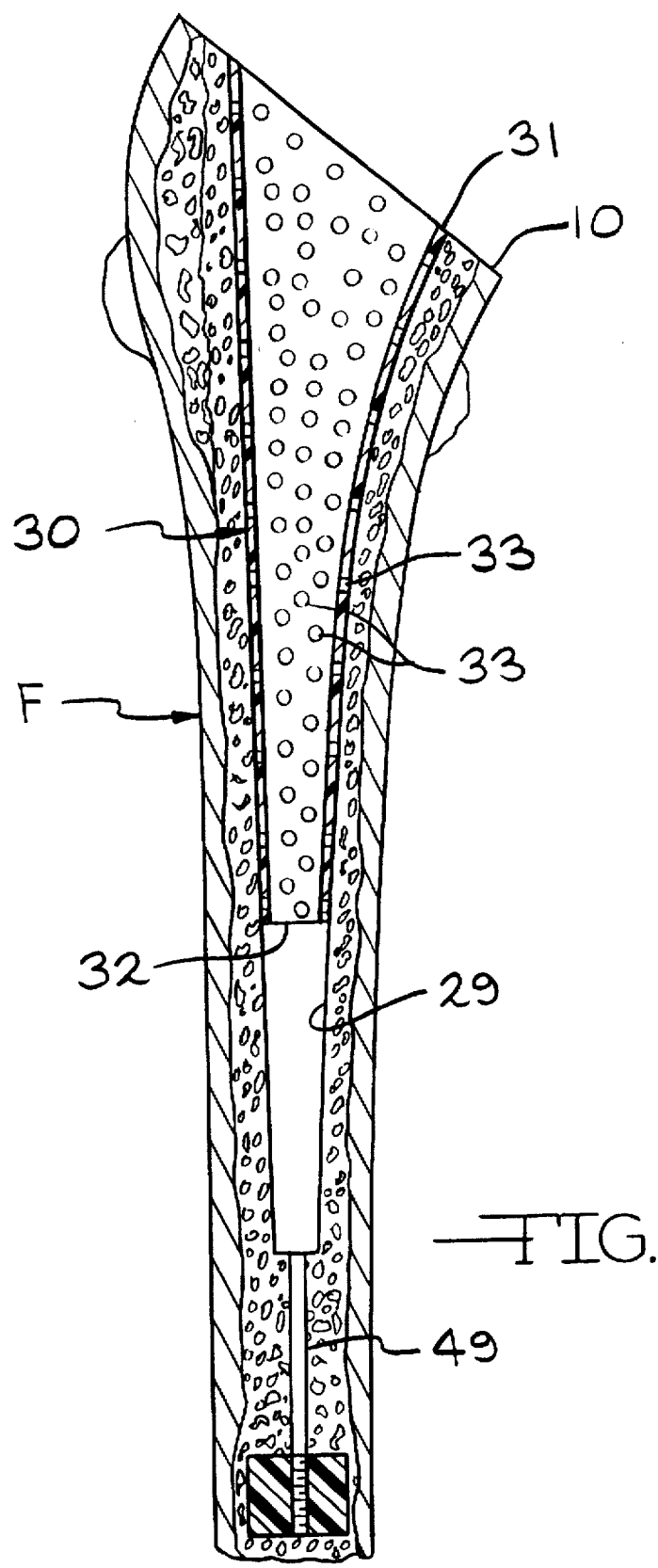
FIG. 7 is an elevational view, in section, showing the preformed sleeve positioned in the prepared cavity.

Upon positioning of the sleeve 30 in the compacted cavity 29, the tamp T' and guide wire 18 are removed leaving the sleeve 30 and the plug cement restrictor 16 in place. (See FIG. 7). If the sleeve 30 was formed according to the alternative embodiment with the extension 39, the extension 39 may be trimmed by the surgeon so that the proximal end 31 of the sleeve 30 is flush with proximal end 10 of the prepared femur F. Preferably it is trimmed using a knife while the tamp T' is still positioned therein to provide support to the sleeve 30 from inward deflection upon the surgeon applying pressure with the knife.

Referring now to FIG. 8, the compacted cavity 29 is now ready to receive the new bone cement in which the prosthesis P will be implanted. The bone cement 42 should be injected under pressure into the compacted cavity 29 after positioning of the sleeve therein. Prior to injecting the new bone cement, the sleeve 30 should be cleaned of any blood, marrow fat or other fluids and dried so that there is no fluid medium between the sleeve 30 and the fresh bone cement 42 in order to permit the fresh bone cement to bond securely to the sleeve 30 forming virtually a single inseparable layer. The injection of bone cement into the prepared cavity may be done by a number of methods widely known in the art. U.S. Pat. Nos. 4,815,454 and 4,896,662 show various types of sealing devices and apparatus for injecting bone cement.

As shown in FIG. 8, a sealing device 44 has a shape permitting it to be sealingly engaged with the proximal end 31 of the sleeve 30. The sealing device 44 is preferably formed of a resilient rubber and the injector apparatus includes a tubular nozzle 46 to which a cartridge 48 containing bone cement 42 may be attached. The tubular nozzle includes a port 47 through which the bone cement 42 may be injected under pressure from the cartridge 48 into the compacted cavity 29.

Upon effecting a seal between the sealing device 44 and the proximal end 10 of the prepared femur with the compacted cavity 29 and the sleeve 30 positioned therein as shown in FIG. 8, bone cement 42 is injected under pressure from the cartridge 48 and into the cavity. As a result of such injection of bone cement 42 under pressure, the bone cement will fill all openings and void areas. Thus, the bone cement will pass through the apertures 33 as shown by arrows 55 and into any void space which may be present between the sleeve 30 and the bone graft 20 defining the compacted cavity 29. The pressure is such that the bone cement 42 will also penetrate into the bone graft 20 to provide a bone/cement interface to securely hold the bone cement in the compacted cavity 29. As may be seen in FIG. 8, the bone cement also flows into the bore 49 left upon removal of the guide wire 18.

Referring now to FIGS. 9 and 10, following injection of the bone cement 42 into the compacted cavity 29, the sealing device 44, nozzle 46 and cartridge 48 are removed and the hip joint prosthesis P is promptly inserted therein prior to the bone cement having time to set and harden. Prior to insertion of the prosthesis P in the cement filled compacted cavity 29, a centralizer 50 manufactured of PMMA or other plastic or bio-compatible material is secured to the distal end 25 of the prosthesis P. The centralizer 50 has an exterior surface 51 of a size radially which permits it to be introduced through the opening at the distal end 32 of the sleeve 30. As is well known in the art, the centralizer 50 includes a closed distal end 52 and a cavity 53 between such closed distal end 52 and the distal end 25 of the prosthesis P to allow a space permitting subsidence of the prosthesis P within the bone cement 42.

As may be seen from FIGS. 9 and 10, the stem 24 of the prosthesis P is sized such that when properly implanted within the bone cement 42, there will be a thickness of such bone cement on the order of 2 to 3 mm between the stem 24 and the interior surface 35 of the sleeve 30 throughout the length of the sleeve from the proximal end 31 to its distal end 32. As previously indicated, the distal end 32 of the sleeve is spaced from the distal end 25 of the prosthesis P a sufficient distance to provide an opening at such distal end 32 sufficiently large to permit the centralizer 50 to pass therethrough.

Figures 11, 12, 13:
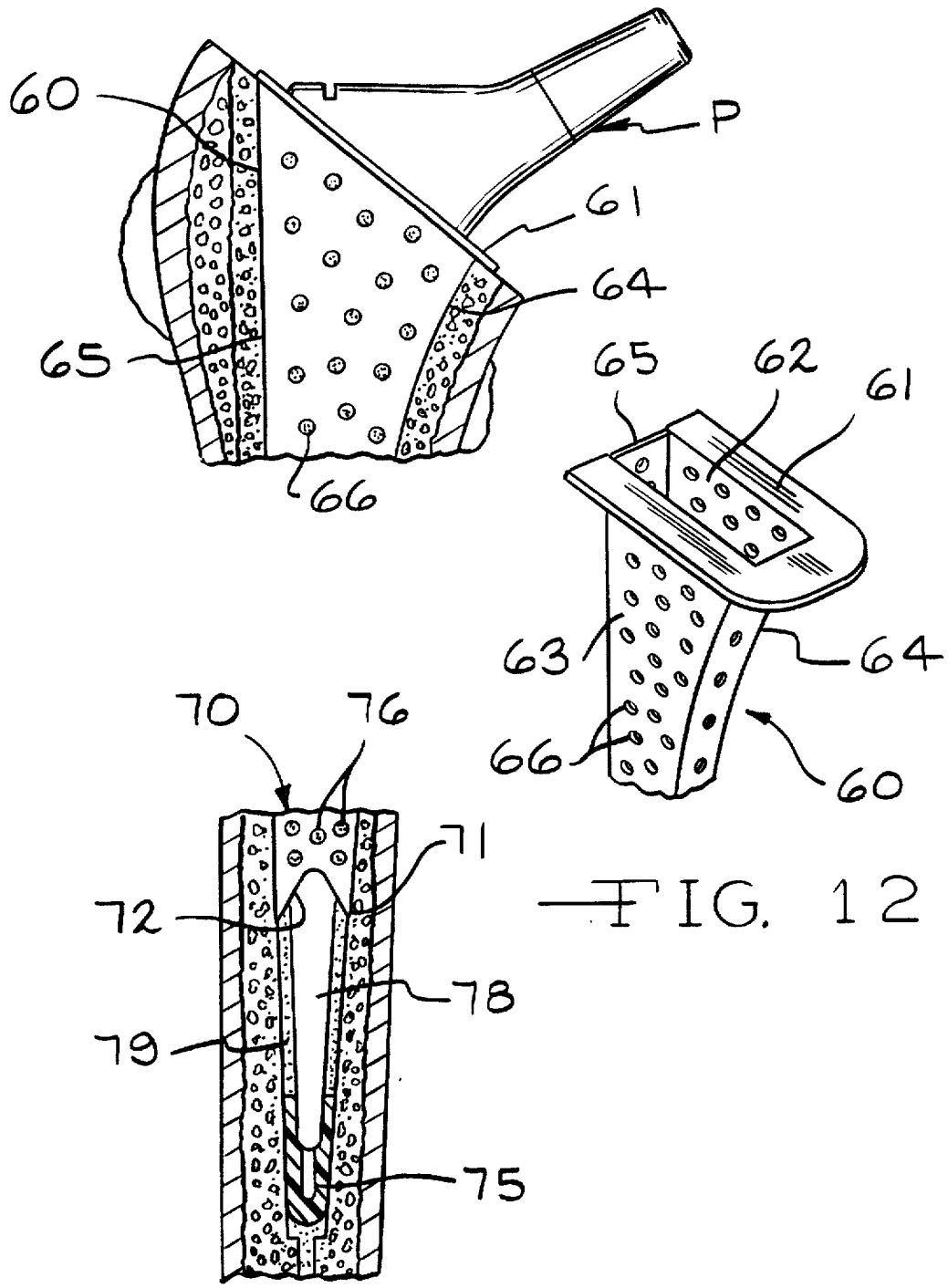
FIG. 11 is a fragmentary elevational view, partly in section, showing a femoral hip joint prosthesis implanted in a prepared femoral cavity with a modified sleeve having a proximal flange.
FIG. 12 is a partial perspective of the modified sleeve.
FIG. 13 is a fragmentary sectional view of the distal end of an implanted femoral hip joint prosthesis and sleeve having a modified distal end configuration.

Referring now to FIGS. 11 and 12, there is shown a modified sleeve 60 which is similar to the sleeve 30 except it is provided with an outwardly extending flange 61 at its proximal end. The sleeve 60 has an interior surface 62, posterior surface 63, medial surface 64 and lateral surface 65 which, upon implantation will face corresponding portions of the femur F as is well known in the art. The flange 61 extends outwardly from the interior surface 62, posterior surface 63 and medial surface 64 of the sleeve 60. As can be seen in FIGS. 11 and 12, the lateral surface 65 of the sleeve 60 does not have a flange extending outwardly away from the lateral surface 65. The flange 61 is trimmable and may thus be trimmed by the surgeon for optimum placement for the specific patient. As in the previous embodiment, the sleeve 60 is provided with apertures 66 sized to permit bone cement to flow therethrough under pressure.

Referring to FIG. 13, there is shown a modified embodiment of sleeve 70 in which the distal end 71 is provided with one or, preferably, a series of V-shaped notches 72. The presence of one or more V-shaped notches permits the insertion of a centralizer 75 of larger radial extent than would be possible without such V-shaped notches 72 as the notches 72 permit deflection of the distal portions of the sleeve 70 between such notches 72 by such radially larger centralizer 75. As in the previous embodiments, the centralizer 70 has apertures 76. In FIG. 13, the stem 78 of the prosthesis is shown as having its distal end received in the centralizer 70 with bone cement 79 encircling such stem.

Figure 14:
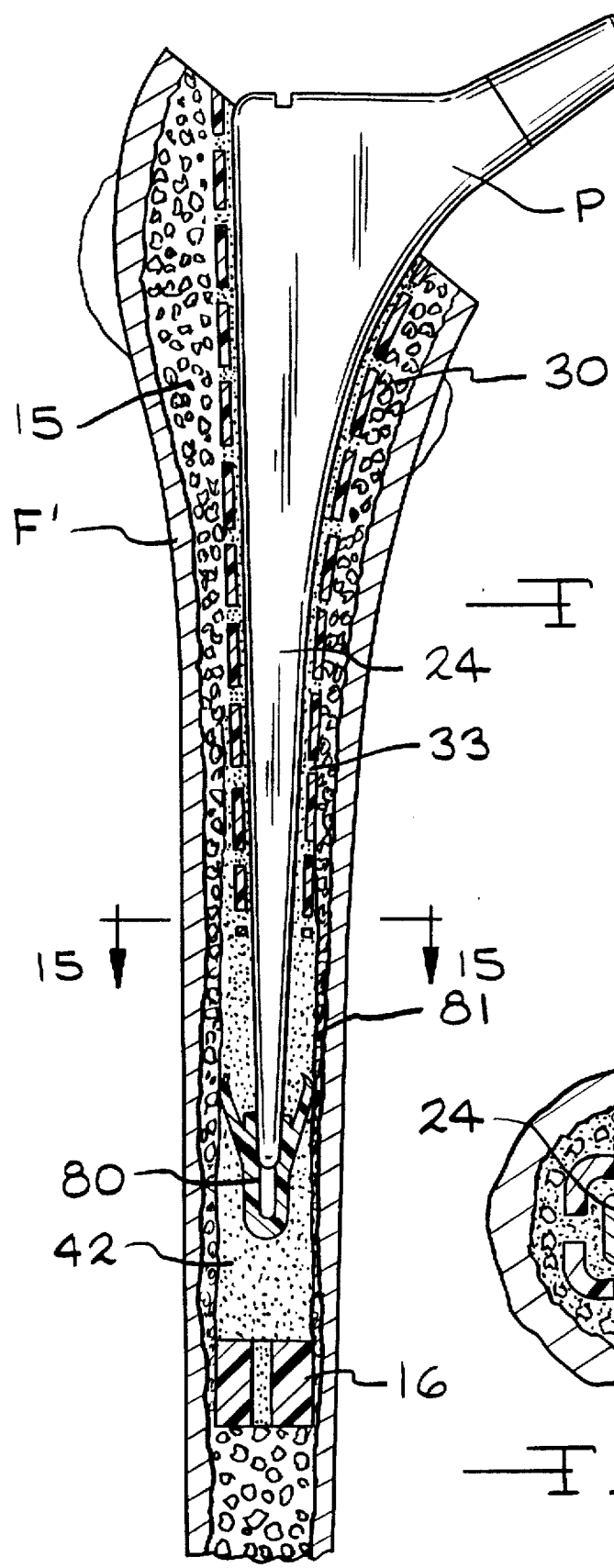
FIG. 14 is an elevational view, partly in section, showing a femoral hip joint prosthesis implanted with a preformed sleeve and fresh pressurized bone cement in primary surgery.
Figure 15:
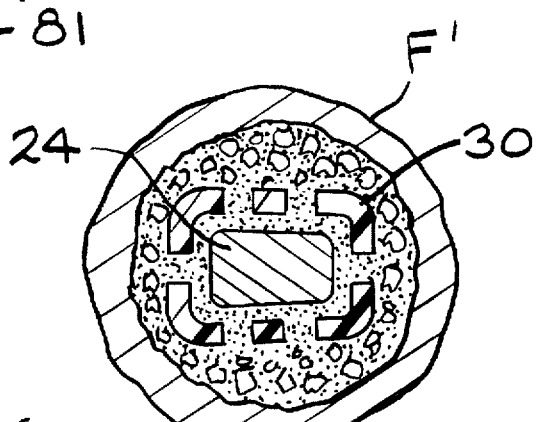
FIG. 15 is a sectional view taken through line 15-15 of FIG. 14.

Referring now to FIGS. 14 and 15, there is shown a prosthesis P implanted in a femur F' as part of primary surgery rather than revision surgery. The same sleeve 30 as utilized in the embodiment of FIGS. 3 through 10 may be utilized. Since the femur F' was prepared for primary as opposed to revision surgery, the cavity 81, which was prepared by the surgeon using an oversized broach, is the appropriate size for receiving the sleeve 30 and prosthesis P with bone cement 42 and centralizer 80. Accordingly, there is no need for the introduction of cancellous bone graft and the sleeve 30, upon insertion in the cavity 81, will be in direct contact with the preserved and stable cancellous bone lining the femoral cortex 15. Stable cancellous bone should not be completely removed but should have at least some preserved for osseointegration with the bone cement introduced under pressure.

Following preparation of the cavity 81, insertion of the plug cement restrictor 16 and sleeve 30 and cleaning and drying of the cavity 81 and sleeve 30, the bone cement 42 is injected into the cavity 81 under pressure as in the previous embodiments. This causes the bone cement 42 to flow into all openings and voids including through the apertures 33 of the sleeve 30 and any void spaces between the sleeve 30 and the femoral cortex. Following introduction of the bone cement 42, the prosthesis P with the centralizer 80 attached to its distal end may be inserted for implantation. The centralizer 80 may have wings 82. As in the previous embodiment, approximately 2 to 3 mm of new bone cement 42 separates the exterior surface of the prosthesis stem 24 from the interior surface of the sleeve 30.

The present invention can be used with hip joint prostheses having a wide variety of stem designs, materials and shapes, collarless or collared, uncoated or pre-coated (such as a hydroxy-apatite coated stem and PMMA coated stems) polished or textured. Since the sleeve is designed to be larger than the stem, a specific size and design of sleeve can be used with a number of different sizes of stems and slightly different shapes of stems. Additionally, many patients, particularly ones with osteoporosis, have bowed or double-curved femurs. Utilization of the sleeve as described herein insures that there will be a minimum of 2 to 3 mm of bone cement around the implanted stem even in those patients having bowed or double-curved femurs.

Many modifications will become readily apparent. The scope of the present invention should be determined only by the scope of appended claims.

I claim:

1. A method for implanting a femoral hip joint prosthesis having a stem extending to a distal end comprising the steps of:

(a) preparing a cavity in the intramedullary canal of a femur, said cavity extending from a proximal end to a distal end;

(b) providing a preformed sleeve having a size permitting its positioning in said prepared cavity, said sleeve having wall portions extending from a proximal end to a distal end, said wall portions having apertures and an interior surface;

(c) positioning said sleeve in said cavity and thereafter;

(d) injecting bone cement under pressure into said cavity and against said interior surface to cause said bone cement to flow through said apertures and to substantially fill all portions thereof; and (e) positioning said prosthesis in said bone cement.

2. The method according to claim 1, wherein said apertures have a size of 1 mm to 3 mm and said sleeve walls have a thickness in the range of 0.5 to 1.5 mm.

3. The method according to claim 1, wherein said preformed sleeve is formed of substantially same material as said bone cement and further including the step of cleaning and substantially drying said sleeve prior to step (d).

4. The method according to claim 3, wherein said stem is in spaced relationship with said sleeve.

5. The method according to claim 4, wherein the thickness of bone cement and said sleeve is in the range of 2 to 3 mm.

6. The method according to claim 1, wherein said positioning of step (c) leaves a portion of said sleeve adjacent said proximal end extending out of said cavity and further including the step of removing said portion.

7. The method according to claim 1, wherein said sleeve has a flange at said proximal end extending outwardly from said wall portions and, upon said positioning of step (c), said flange is adjacent said cavity proximal end.

8. The method according to claim 1, wherein said sleeve distal end defines an opening and said prosthesis stem extends through said opening.

9. The method according to claim 8, wherein a centralizer is positioned on said stem distal end and passes through said sleeve opening upon positioning said prosthesis.

10. The method according to claim 9, wherein said centralizer has a size larger than said opening and said sleeve has notches adjacent distal end and the portions of said sleeve between said notches expand outwardly upon said centralizer passing therethrough.

11. The method according to claim 1, further including providing a tamp having an exterior surface portion conforming to said sleeve interior surface, said sleeve being affixed to said tamp during step (c).

12. A method for implanting a femoral hip joint prosthesis having a stem comprising the steps of:

(a) preparing a cavity in the intramedullary canal of a femur, said cavity being defined by a wall extending from a proximal end toward a distal end;

(b) providing a preformed sleeve having a size permitting its positioning in said prepared cavity, said sleeve having wall portions extending from a proximal end to a distal end, each of said wall portions having an exterior surface, an interior surface and apertures extending through said wall portions;

(c) positioning said sleeve in said cavity with portions of said exterior surface in contact with said cavity wall, and other portions spaced from said cavity wall and thereafter;

(d) injecting bone cement under pressure into said cavity and against said interior surface to cause said bone cement to flow through said apertures and to substantially fill said spaces between said sleeve and said cavity wall; and (e) positioning said prosthesis in said bone cement with said stem in generally spaced relationship with said interior surface.

13. The method according to claim 12, wherein said apertures have a size of 1 mm to 3 mm and said sleeve walls have a thickness in the range of 0.5 to 2 mm.

14. The method according to claim 12, wherein said preformed sleeve is formed of substantially same material as said bone cement and further including the step of cleaning and substantially drying said sleeve prior to the introduction of bone cement.

15. The method according to claim 12, wherein the thickness of bone cement and said sleeve is in the range of 2 to 3 mm.

16. The method according to claim 12, wherein said positioning of step (c) leaves a portion of said sleeve adjacent said proximal end extending out of said cavity and further including the step of removing said portion.

17. The method according to claim 12, wherein said sleeve has a flange at said proximal end extending outwardly from said wall portions and, upon said positioning of step (c), said flange is adjacent said cavity proximal end.

18. The method according to claim 12, wherein said sleeve distal end defines an opening and said prosthesis stem extends through said opening.

19. The method according to claim 18, wherein a centralizer is positioned on said stem distal end and passes through said sleeve opening upon positioning said prosthesis.

20. The method according to claim 19, wherein said centralizer has a size larger than said opening and said sleeve has notches adjacent distal end and the portions of said sleeve between said notches expand outwardly upon said centralizer passing therethrough.

21. The method according to claim 12, further including providing a tamp having an exterior surface portion conforming to said sleeve interior surface, said sleeve being affixed to said tamp during step (c).

22. In combination, (a) a femoral hip joint prosthesis having an elongated stem extending to a distal end adapted to be implanted in a femoral canal, (b) a sleeve disposed in spaced relationship with said stem, said sleeve having wall portions extending from a proximal and to a distal end and being formed of bone cement and having apertures formed therein and (c) bone cement between said sleeve and said stem, said bone cement extending through said apertures, substantially all portions of said sleeve being in spaced relationship with said elongated stem.

23. The combination according to claim 22, wherein said sleeve has a wall portion having a thickness of 0.5 to 2 mm.

24. The combination according to claim 22, wherein said sleeve is formed of substantially the same material as said bone cement and is adhered thereto.

25. The combination according to claim 24, wherein the thickness of said sleeve and adhered bone cement in the area of said sleeve distal end is in the range of 2 to 3 mm.

26. The combination according to claim 22, wherein said sleeve has a flange at said proximal end extending outwardly from said wall portions.

27. The combination according to claim 22, wherein said sleeve distal end defines an opening and said prosthesis stem extends through said opening.

28. The combination according to claim 27, wherein a centralizer is positioned on said stem distal end.

29. The combination according to claim 27, wherein said centralizer has a size larger than said opening and said sleeve has notches adjacent distal end and the portions of said sleeve between said notches are adapted to expand outwardly upon said centralizer passing therethrough.

* * * * *